(12) United States Patent  (10) Patent No.: US 8,828,015 B2
Green, II et al.  (45) Date of Patent: *Sep. 9, 2014

(54) ADJUSTABLE FEMORAL RESECTION GUIDE

(71) Applicant: MicroPort Orthopedics Holdings Inc., Tiel (NO)

(72) Inventors: John Michael Green, II, Arlington, TN (US); David Bradford Harness, Eads, TN (US)

(73) Assignee: Microport Orthopedics Holdings Inc., Tiel (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/943,384

(22) Filed: Jul. 16, 2013

(65) Prior Publication Data

US 2013/0304071 A1  Nov. 14, 2013

Related U.S. Application Data

(63) Continuation of application No. 13/658,351, filed on Oct. 23, 2012, now Pat. No. 8,523,870, and a continuation of application No. 12/544,279, filed on Aug. 20, 2009, now Pat. No. 8,313,491.

(51) Int. Cl.
 *A61B 17/15* (2006.01)

(52) U.S. Cl.
 CPC .................................. *A61B 17/155* (2013.01)
 USPC ........................................................ 606/88

(58) Field of Classification Search
 USPC .............................. 606/82, 86 R–90, 102, 105
 See application file for complete search history.

(56) References Cited

U.S. PATENT DOCUMENTS

| 4,926,847 | A | 5/1990 | Luckman |
| 5,486,178 | A | 1/1996 | Hodge |
| 5,662,656 | A | 9/1997 | White |
| 5,709,689 | A | 1/1998 | Ferrante et al. |
| 5,810,831 | A | 9/1998 | D'Antonio |
| 6,013,081 | A | 1/2000 | Burkinshaw et al. |
| 6,059,788 | A | 5/2000 | Katz |
| 6,440,140 | B2 | 8/2002 | Bullivant et al. |
| 6,500,179 | B1 | 12/2002 | Masini |
| 7,182,767 | B2 | 2/2007 | Canonaco et al. |
| 8,313,491 | B2 * | 11/2012 | Green et al. ............... 606/88 |
| 8,523,870 | B2 * | 9/2013 | Green et al. ............... 606/88 |
| 2006/0142778 | A1 | 6/2006 | Dees, Jr. |
| 2006/0217734 | A1 | 9/2006 | Sanford et al. |
| 2007/0123900 | A1 | 5/2007 | Canonaco et al. |
| 2007/0173851 | A1 | 7/2007 | McMillen et al. |

(Continued)

FOREIGN PATENT DOCUMENTS

EP  0 121 780  10/1984

*Primary Examiner* — Michael T Schaper
(74) *Attorney, Agent, or Firm* — Duane Morris LLP

(57) ABSTRACT

A chamfer resection guide assembly for effecting chamfer cuts into a resected distal surface of a femur in connection with a distal total knee implant has an anchor member configured for anterior referencing of the chamfer cuts, a block member including one or more cutting guide slots for guiding a cutting tool for making chamfer resections and a camming member. The camming member operably connects the block member and the anchor member and the position of the block member with respect to the anchor member is adjusted by operation of the camming member thus allowing adjustment of the position of the cutting guide slots with respect to the anchoring member.

11 Claims, 12 Drawing Sheets

(56) References Cited

U.S. PATENT DOCUMENTS

2007/0233140 A1 10/2007 Metzger et al.
2008/0161824 A1 7/2008 McMillen
2010/0324563 A1 12/2010 Green et al.

* cited by examiner

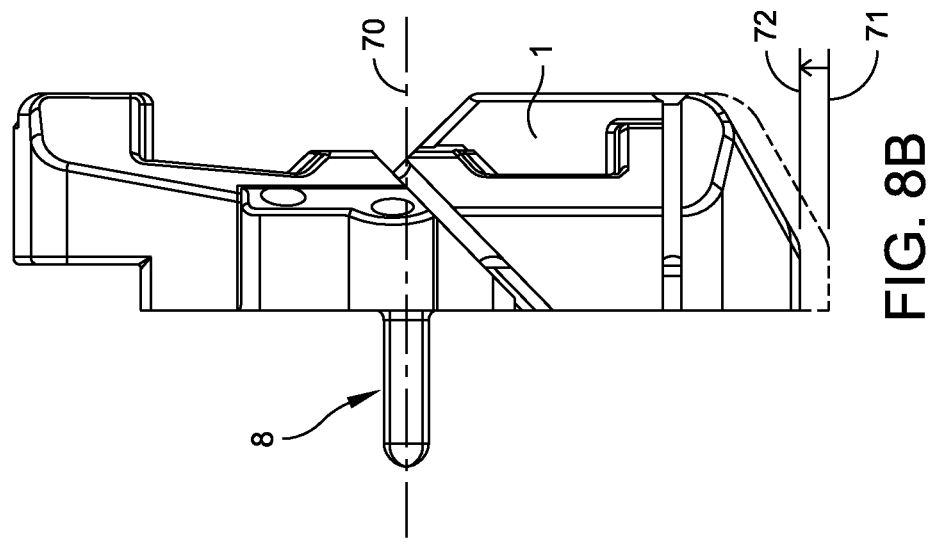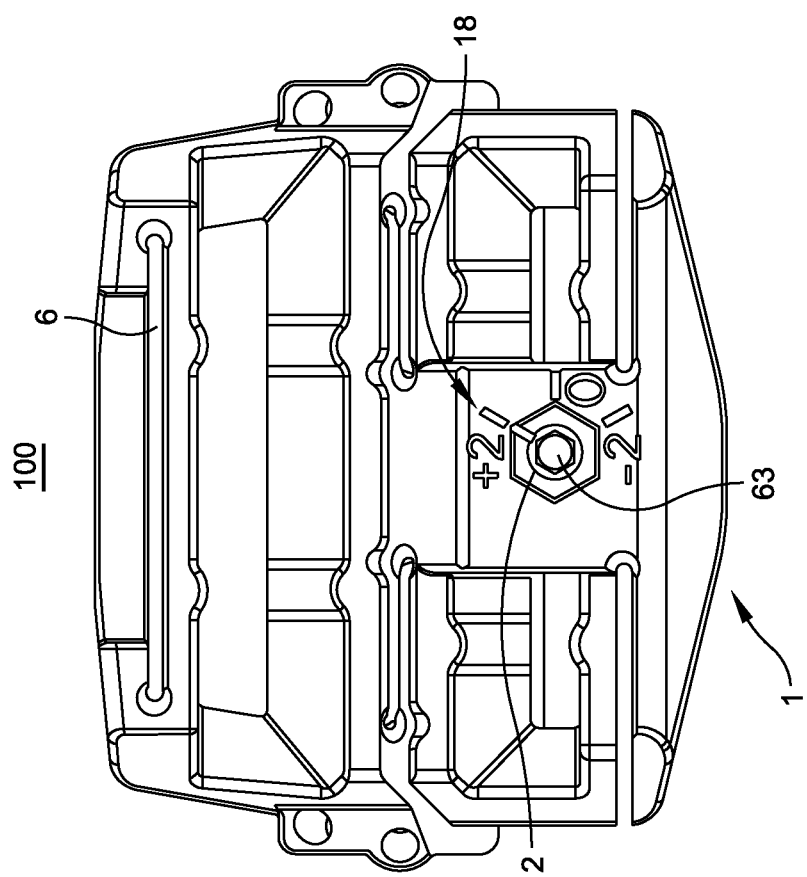

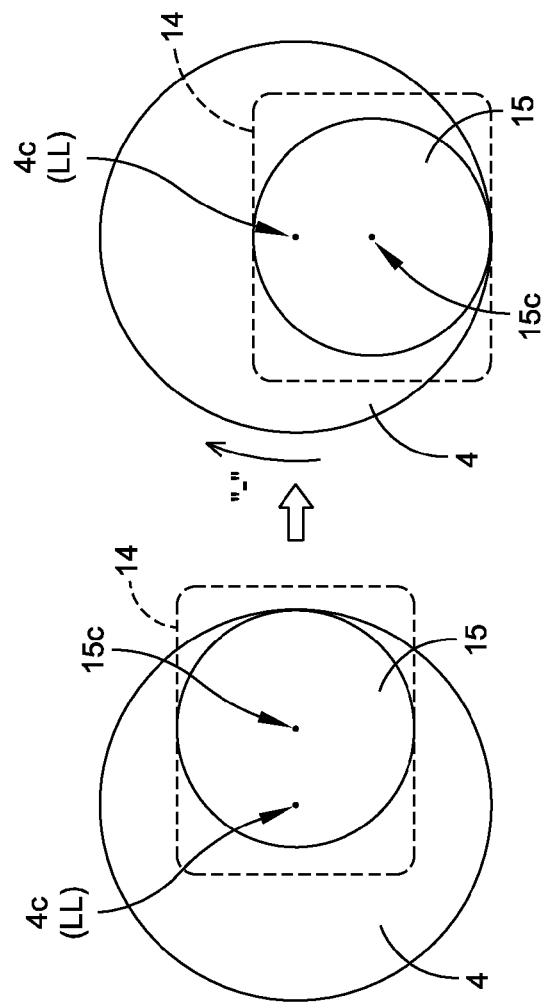
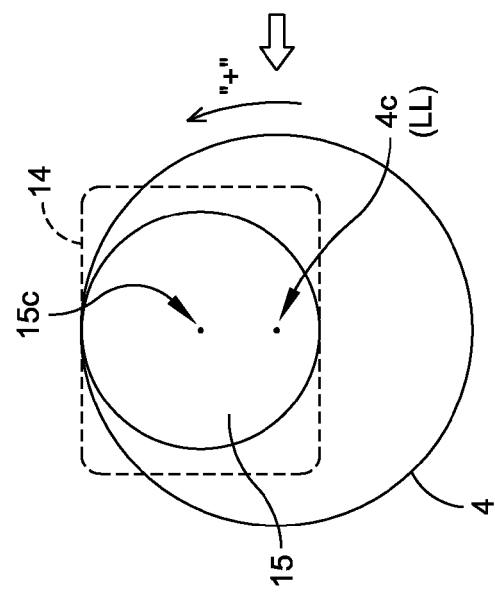
FIG. 11C  FIG. 11A  FIG. 11B

ADJUSTABLE FEMORAL RESECTION GUIDE

CROSS-REFERENCE TO RELATED APPLICATIONS

This application is a continuation of U.S. patent application Ser. No. 13/658,351, filed on Oct. 23, 2012, now U.S. Pat. No. 8,523,870 issued on Sep. 3, 2013, which is a continuation of U.S. patent application Ser. No. 12/544,279, filed on Aug. 20, 2009, now U.S. Pat. No. 8,313,491 issued on Nov. 20, 2012, the disclosures of which are incorporated herein by reference in their entirety.

FIELD OF THE INVENTION

The present disclosure is related to bone chamfer resection guides use for performing chamfer or bevel resections at the distal end of a femur in connection with distal femoral total knee implant surgery.

BACKGROUND

Chamfer resection guides are used in orthopedic surgery for resecting the distal end of the femur. Currently available chamfer resection guides are monolithic instruments and are secured to a distal femoral resection by means of either pins or orthogonal flange protruding from the distal face of the instrument. Once the instrument is coupled to the distal femur and its position is established, adjustment of the instrument requires that the chamfer resection guide is removed and its reference features are repositioned by some other means. These features typically are either holes in the distal femur, or a rough anterior resection.

Other devices used to refine the final position of he chamfer resection guide and subsequently the implant are used in steps either prior to choosing the best size chamfer resection guide (a step known as sizing the femur) using a femoral caliper or by removing the chamfer resection guide altogether and using another device to relocate the referencing features that the chamfer guide was attached to.

A chamfer resection guide is the best instrument for checking the final position of the resections before making the resections. This is because the resections are made through the guide, so a reference plane (i.e. a bladerunner) can be placed through the guide to re-check the resection levels. Instruments that attempt to refine the final position of the chamfer guide without the guide in place does not provide the user an accurate means of verifying the resection levels of the final implant. Additionally, if the chamfer resection guide does need to be repositioned, removal of the guide and adjustments of its referencing features takes additional time and induces a chance for additional error.

SUMMARY

According to an embodiment of the present disclosure a chamfer resection guide assembly for a distal total knee implant is disclosed. The chamfer resection guide assembly comprises an anchor member for attaching to a resected distal surface of a femur, a block member including one or more cutting guide slots and a femoral contacting surface for placement against the resected distal surface of the femur, and a camming member. The femoral contacting surface of the block member is provided with a recessed region in which the anchor member is slidably engaged therein. The camming member operably connects the block member and the anchor member and is configured for linearly displacing the anchor member and the block member with respect to each other for adjusting the position of the block member with respect to the femur when the anchor member is attached to the distal resection of the femur.

A chamfer resection guide assembly for effecting chamfer cuts into a resected distal surface of a femur in connection with a distal total knee implant, the chamfer resection guide assembly having an anterior end and comprising:
  an anchor member configured for anterior referencing of the chamfer cuts;
  a block member including one or more cutting guide slots and a femoral contacting surface for placement against the resected distal surface of the femur, wherein the femoral contacting surface is provided with a recessed region in which the anchor member is slidably engaged therein,
  wherein the anchor member comprises a second femoral contacting surface and a footplate extension that extends from the second femoral contacting surface near the anterior end of the chamfer resection guide assembly; and
  a camming member operably connecting the block member and the anchor member and configured for linearly displacing the anchor member and the block member with respect to each other by a camming action;
  wherein the block member is provided with a blind hole provided in the recessed region and the anchor member is provided with a blind slot, wherein the camming member is captured between the block member and the anchor member by engaging the blind hole and the blind slot, whereby turning the camming member about its longitudinal axis produces the camming action;
  wherein the camming member comprises:
    a first end engaging the blind hole of the block member;
    a second end engaging the blind slot of the anchor member; and
    an elastically compressible member contained between the first end and the second end and urging the first end against the block member and the second end against the anchor member.

The chamfer resection guide assembly of the present disclosure is configured so that the position of the chamfer resection guide attached to the distal end of a femur can be adjusted without removing the chamfer resection guide assembly from the distal end of the femur.

BRIEF DESCRIPTION OF THE DRAWINGS

FIGS. 8A-8B are a plan view and a side view of the chamfer resection guide assembly 100 in a "+" position setting.

FIGS. 11A-11C are schematic illustration of the camming action provided by the cam body 4 and the offset cylinder boss 15 of the camming member 20.

The features shown in the above referenced drawings are illustrated schematically and are not intended to be drawn to scale nor are they intended to be shown in precise positional relationship. Like reference numbers indicate like elements.

DETAILED DESCRIPTION

Figure 1:
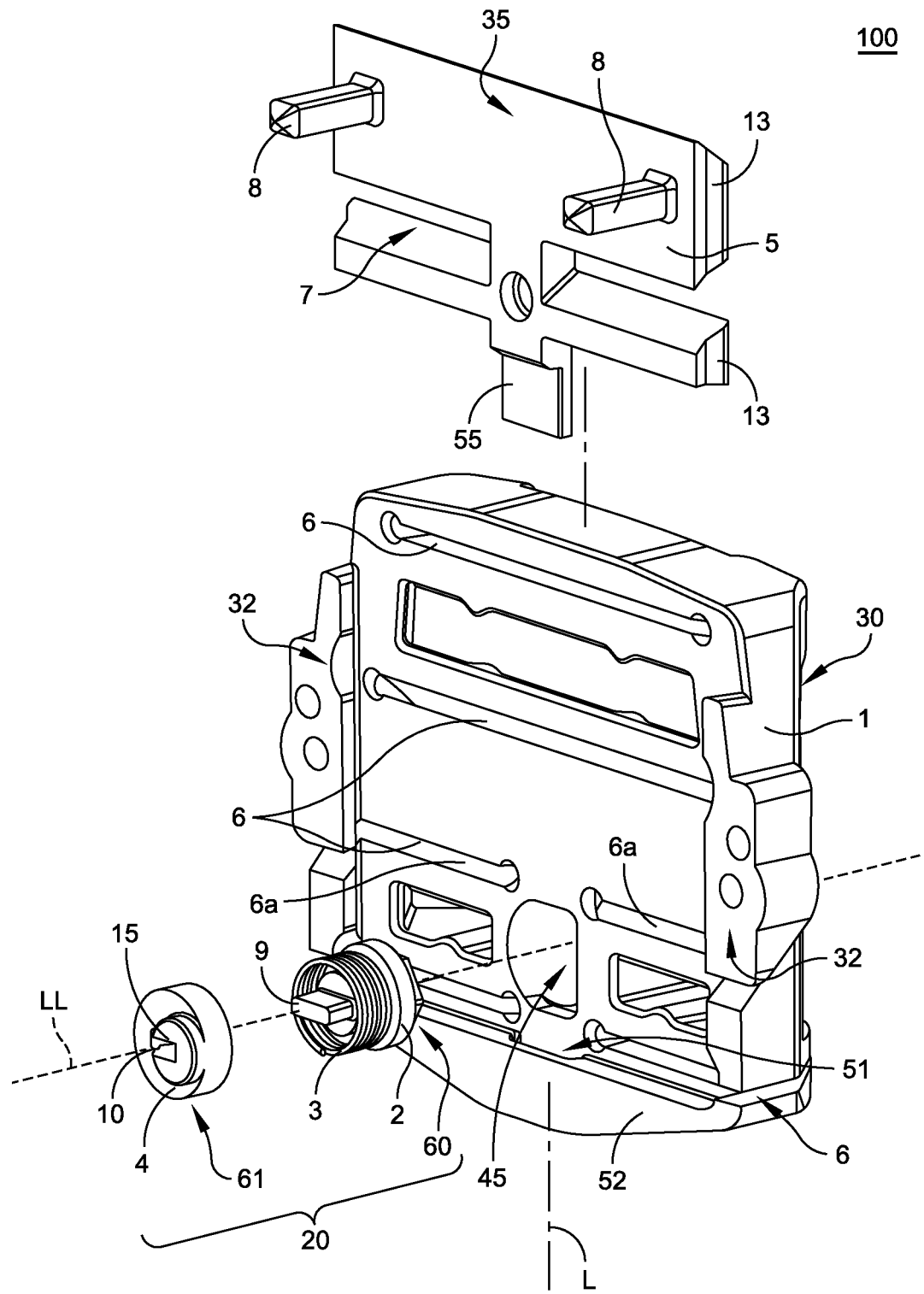
FIG. 1 is an exploded isometric view of the components of a chamfer resection guide assembly 100 according to an embodiment of the present disclosure.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, such as "coupled", "connected" and "interconnected," refer to a relationship wherein structures are secured or attached to one another either directly or indirectly through intervening structures, as well as both movable or rigid attachments or relationships, unless expressly described otherwise.

Referring to FIG. 1, an exploded view of an embodiment of a chamfer resection guide assembly 100 is shown. The chamfer resection guide 100 comprises an anchor member 5, a block member 1, and a camming member 20. The anchor member 5 and the block member 1 are slidably engaged to each other and the camming member 20 operatively connects and controls the relative sliding motion of the anchor member 5 and the block member 1. The block member 1 comprises a plurality of slots 6 that function as guiding means for guiding a cutting tool 50 (See FIG. 4) for making various bone resections required for the final femoral implant. An oscillating saw is an example of a cutting tool. Each of the plurality of slots 6 has an appropriate length and extends through the full thickness of the block member 1 at an angle that is appropriate for making a particular resection cut into the distal end of the femur.

Figure 10:
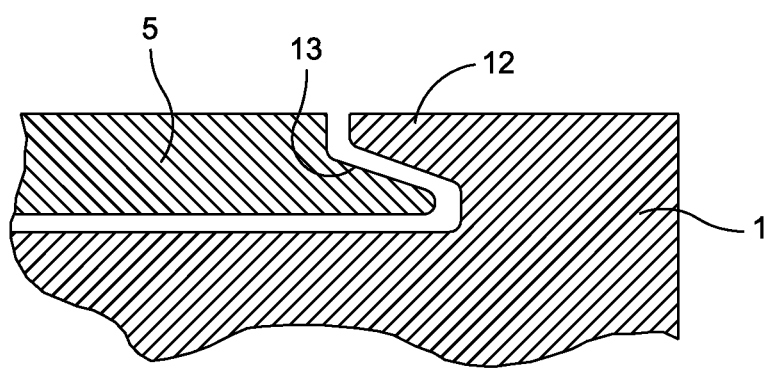
FIG. 10 is a detailed cross-sectional view of the guiderail structures 12 of the block member 1 and the male boss structures 13 of the anchor member 5 in an engaged configuration.

The block member 1 has two major sides: a top side 30, the side that faces away from the femoral bone when in use, and a femoral contacting surface 32 side. The side that faces the femur and has femoral contacting surfaces 32 is attached to the distal resected surface of the femur during use. Provided on the femoral contacting surface 32 of the block member 1 is a recessed region 40 in which the anchor member is slidably engaged therein. The recessed region 40 is cut into the femoral contacting surface 32 and is defined by a pair of guiderail structures 12 for engaging the anchor member 5. The guiderail structures 12 extend parallel to the longitudinal axis L of the chamfer resection guide assembly 100. Thus, the recessed region 40 extends along the longitudinal axis L and allows the anchor member 5 to slide linearly within the recessed region 40 parallel to the longitudinal axis L. To guiderail structures 12 and the anchor member 5 are configured to slidably engage each other while preventing the anchor member 5 from moving in lateral directions (i.e. perpendicular to the longitudinal axis L). For example, in the illustrated embodiment, the guiderail structures 12 are configured to have an undercut profile while the anchor member 5 is provided with corresponding male boss structures 13 along the sides that engage the guiderail structures 12. These engaging structures are shown in detail in the cross-sectional view in FIG. 10. The particular configuration of the guiderail structures 12 and the male boss structures 13 illustrated herein are only examples and other equivalent configurations are within the scope of the current disclosure.

When assembled and situated within the recessed region 40 of the block member 1, the side of the anchor member 5 that faces in the same direction as the femoral contacting surface 32 will be referred to herein as the second femoral contacting surface 35. The anchor member 5 may be provided with an appropriate means for attaching or anchoring to the resected distal surface of the femur. In the illustrated example, two anchoring pins 8 are provided on the second femoral contacting surface 35 of the anchor member 5. The anchoring pins 8 can be inserted into predrilled holes in the femur to attach the anchor member 5 and, thus, the chamfer resection guide assembly 100 to the resected distal surface of the femur.

Figure 3:
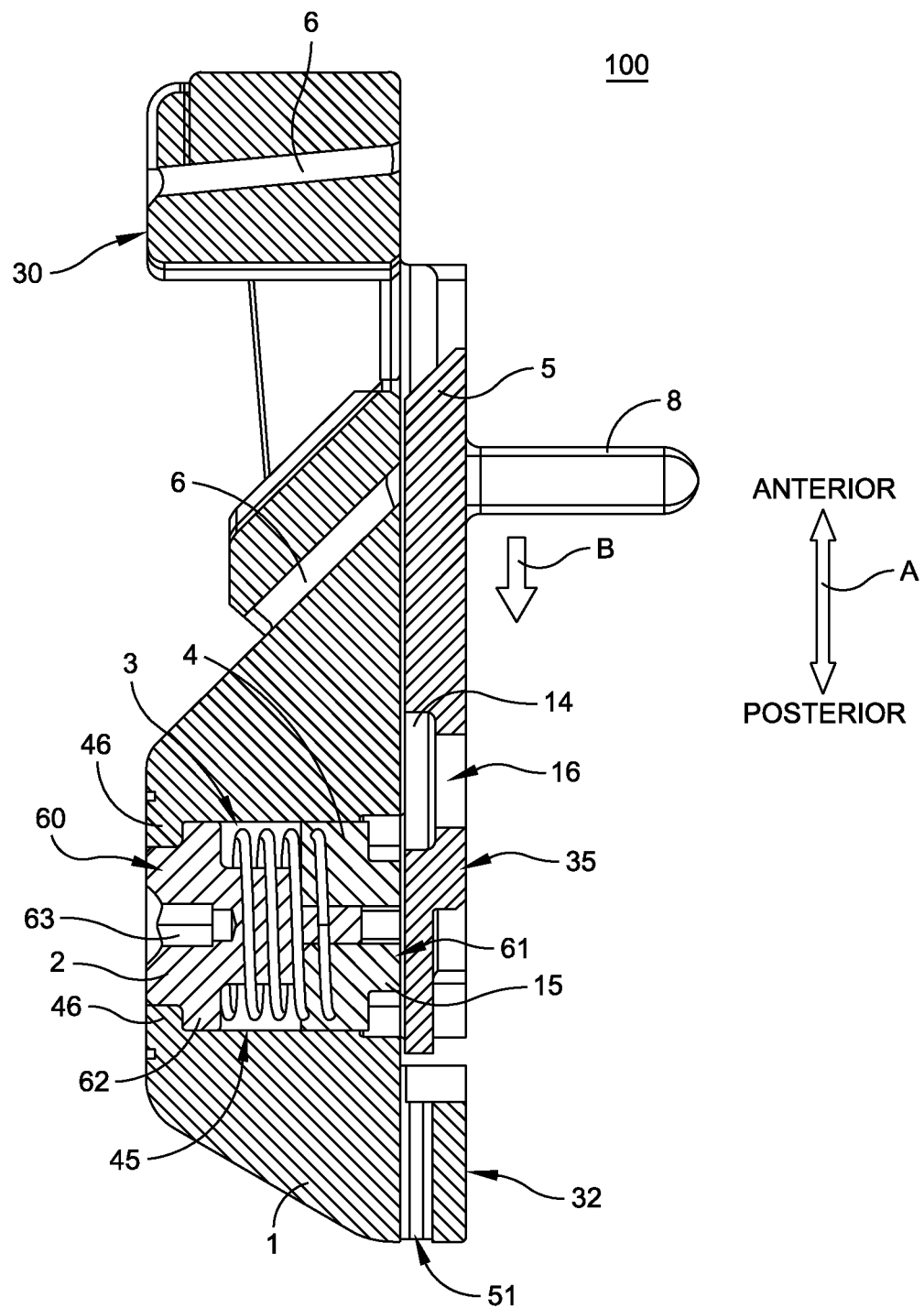
FIG. 3 is a longitudinal cross-sectional view of the chamfer resection guide assembly 100 of FIG. 1 in a partially assembled state.
Figure 4:
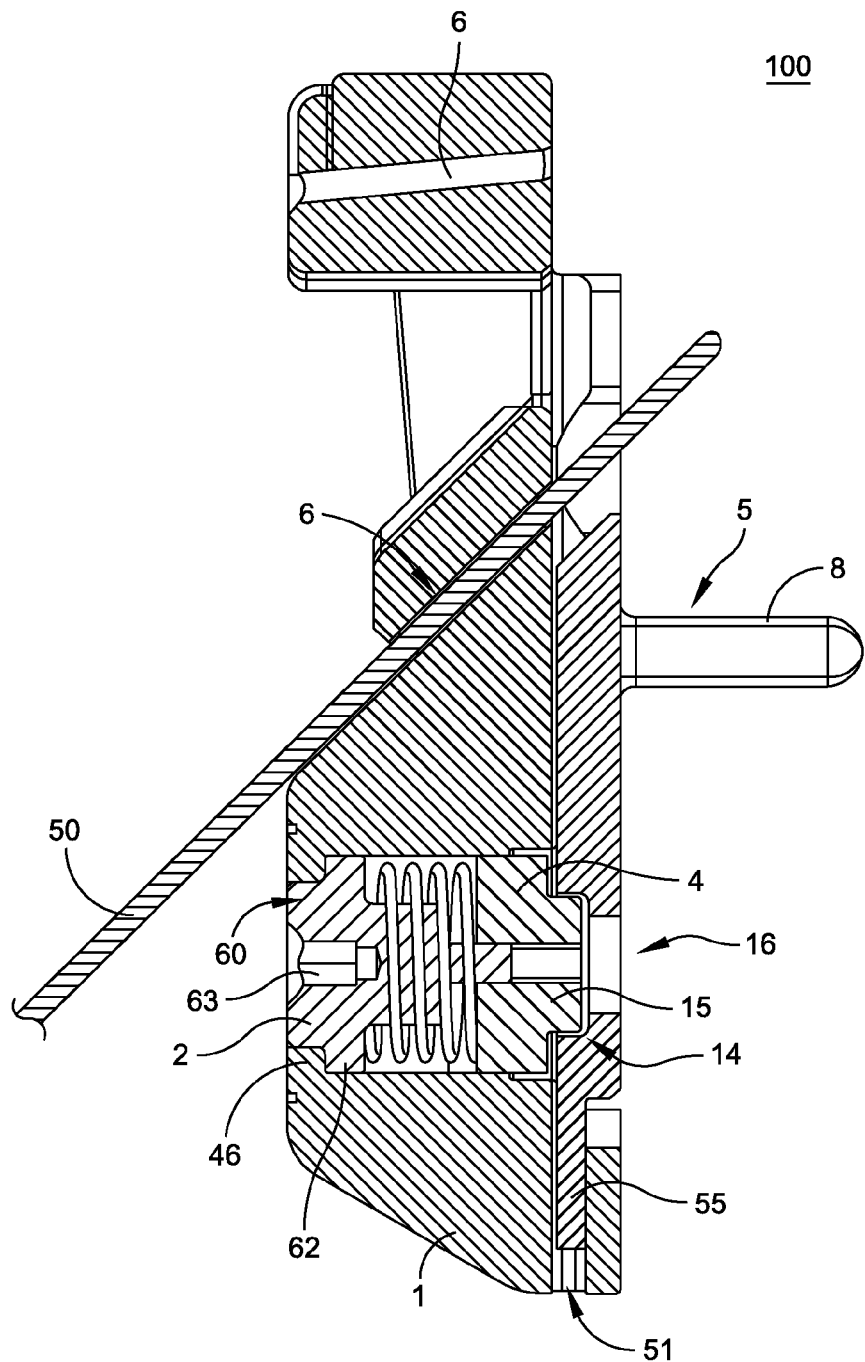
FIG. 4 is a longitudinal cross-sectional view of the chamfer resection guide assembly 100 of FIG. 1 in a fully assembled state.

In the longitudinal cross-sectional view of a fully assembled chamfer resection guiding assembly 100 shown in FIG. 3, the camming member 20 is captured between the anchor member 5 and the block member 1. Thus, the camming member 20 operably connects the anchor member 5 and the block member 1 and enables linear displacement of the block member 1 and the anchor member 5 with respect to each other. Referring to FIGS. 1 and 4, the camming member 20 comprises an adjustment plunger 2, a cam body 4 and a coil spring 3. The adjustment plunger 2 cooperates with the block member 1 and the cam body 4 cooperates with the anchor member 5 to effectuate a linear displacement of the block member 1 with respect to the anchor member 5 by operation of the cam 4.

The adjustment plunger 2 has a first end 60 and a second end 61. The first end 60 of the adjustment plunger 2 is configured for being received into a first blind hole 45 provided in the recessed region 40 and cooperating with the block member 1. The adjustment plunger 2 and the cam body 4 are configured to couple together to rotate about the longitudinal axis LL of the camming member 20 in unison while translating axially with respect to each other. This coupling configuration is achieved by a motise and tenon joint. In the illustrated example, a tenon 9 structure is provided at the second end 61 of the adjustment plunger 2 that mates with a corresponding mortise 10 structure provided in the cam body 4. The mortise and tenon joint transfer rotational loads from the adjustment plunger 2 to the cam body 4 thus allowing them to rotate together while permitting the adjustment plunger 2 to translate axially when the adjustment plunger 2 is pushed towards the cam body 4. It would be equally effective to swap the locations of the mortise 10 and the tenon 9 structures shown in the illustrated example. Alternatively, other functionally equivalent structures can be provided on the cam body 4 and the adjustment plunger 2 to form the coupling.

Figure 2:
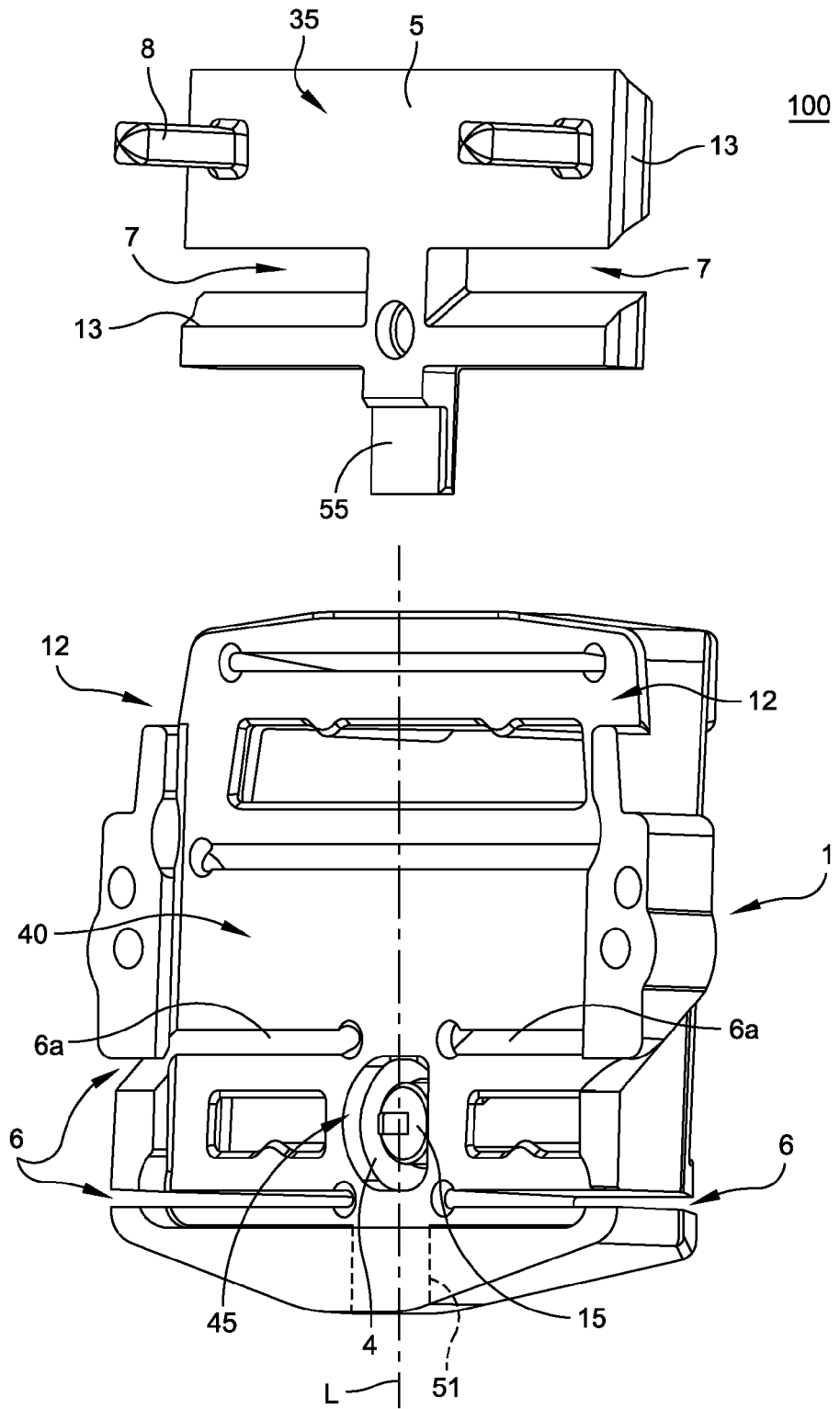
FIG. 2 is another partially exploded isometric view certain components of the chamfer resection guide assembly 100 of FIG. 1.

Referring to FIGS. 1-5, the chamfer resection guide assembly 100 is assembled by first assembling the camming member 20 components into the first blind hole 45 of the block member 1. The adjustment plunger 2 is inserted first into the first blind hole 45 and the coil spring 3 and the cam body 4 are inserted over the adjustment plunger 2 so that the coil spring 3 is contained between the adjustment plunger 2 and the cam body 4. The dimension of the coil spring 3 is such that a portion of the cam body 4 protrudes out of the first blind hole 45. FIG. 2 shows the camming member 20 assembled into the first blind hole 45.

The anchor member 5 is slid into the recessed region 40 of the block member 1 using the guiderail structures 12 as the guide while compressing the camming member 20 assembly into the first blind hole 45. The guiderail structures 12 of the block member 1 engages the male boss structures 13 of the anchor member 5 as discussed above. FIG. 3 shows an interim state where as the anchor member 5 is being slid into the recessed region 40 in the direction of the arrow B. In this interim state, the anchor member 5 is not yet fully inserted into the recessed region 40 and the anchor member 5 is covering the first blind hole 45 compressing the camming member 20 assembly. As the anchor member 5 is further slid into the recessed region 40 a blind slot 14 provided on the anchor member 5 comes in alignment with the camming member 20 and the cam body 4 of the camming member 20 is urged into engagement with the blind slot 14. In this fully assembled state, the camming member 20 assembly is captured between the anchor member 5 and the block member 1 as shown in FIG. 4.

The anchor member 5 is provided with a tab portion 55 that extend longitudinally for engaging the block member 1. The block member 1 is provided with a complementary slot 51 for receiving the tab portion 55. In the fully assembled state shown in FIGS. 4 and 5A, the tab portion 55 is positioned in the slot 51.

The cam body 4 comprises an offset cylinder boss 15 that fits into and engages the blind slot 14 of the anchor member 5. This arrangement allows the chamfer resection guide assembly 100 to be held together as the offset cylinder boss 15 is always urged into the blind slot 14 of the anchor member 5 by the force of the coil spring 3. A through hole 16 may be provided in the anchor member 5 permitting access to the cam body 4 and allowing disassembly of the chamfer resection guide assembly 100. By depressing the cam body 4 through the through hole 16 compressing the coil spring 3, the offset cylinder boss 15 is removed from the blind slot 14 and the anchor member 5 can be removed from the block member 1 for disassembly.

As shown in FIGS. 3 and 4, the anchor member 5 is provided with a blind slot 14 for receiving the offset cylinder boss 15 of the cam body 4. The coil spring 3 is configured to be in compression when the camming member 20 is captured between the anchor member 5 and the block member 1 and urge the cam body 4 and the adjustment plunger 2 outward against the anchor member 5 and the block member 1, respectively. The coil spring 3 may be substituted with any types of elastically compressible member that can provide the equivalent function.

Figure 5A:
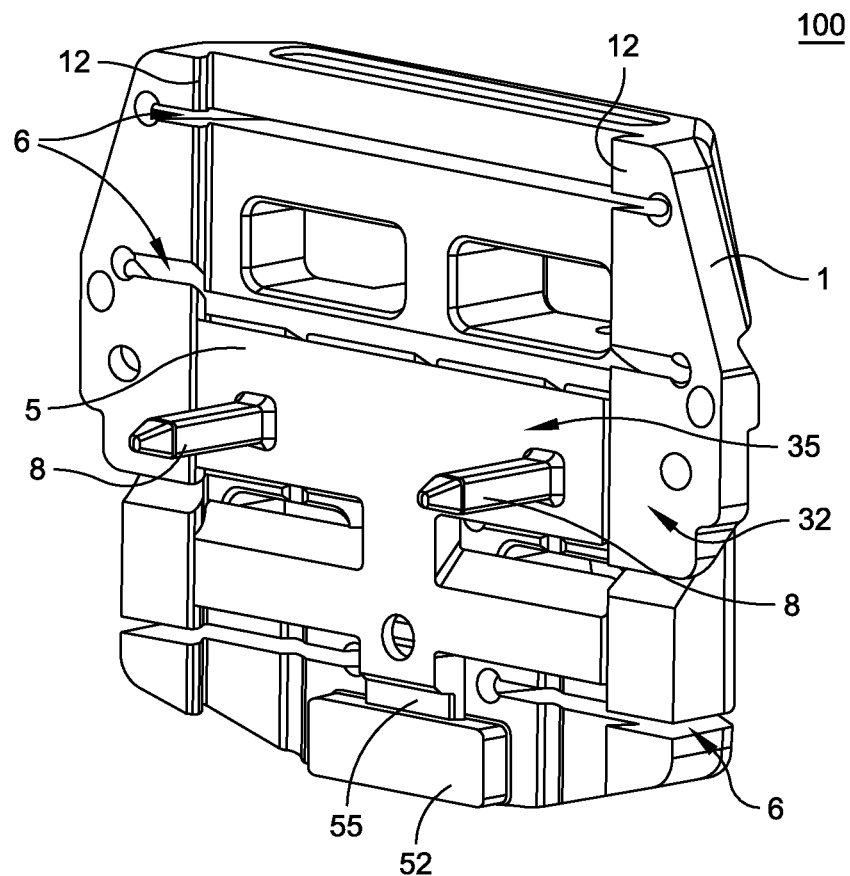
FIG. 5A is an isometric view of a fully assembled chamfer resection guide assembly 100.

As shown in FIGS. 1, 3 and 4, the center of the offset cylinder boss 15 is offset from the center of the cam body 4. The blind slot 14 of the anchor member 5 is sized to receive the offset cylinder boss 15 of the cam body 4. When the camming member 20 is rotated about its longitudinal axis, the offset configuration of the offset cylinder boss 15 allows the offset cylinder boss 15 to act as a cam and move the anchor member 5 and the block member 1 with respect to each other in the anterior or posterior directions as noted by the arrow A. The maximum amount of displacement of the anchor member 5 and the block member 1 with respect to each other is the function of the amount of the offset between the center of the cylinder boss 15 and the center of the cam body 4. FIG. 5A shows a fully assembled configuration of the chamfer resection guide assembly 100.

When the anchor member 5 is attached to the distal femoral resection, the position of the anchor member 5 with respect to the femoral bone will be fixed and the position of the block member 1 with respect to the femoral bone can be adjusted by using the camming member 20. The adjustment plunger 2 and the first blind hole 45 of the block member 1 are configured to allow controlled adjustment of the relative position of the block member 1 with respect to the anchor member 5. In the illustrated example chamfer resection guide assembly 100, the adjustment plunger 2 is configured to have a mid-section 62 that is larger in diameter than the first end 60 and the second end 61, as shown in FIGS. 3 and 4. This mid-section 62 allows the coil spring 3 to be contained between the adjustment plunger 2 and the cam body 4 and interferes with a retaining lip 46 of the first blind hole 45 and retains the adjustment plunger 2 within the first blind hole 45.

Figure 7B:
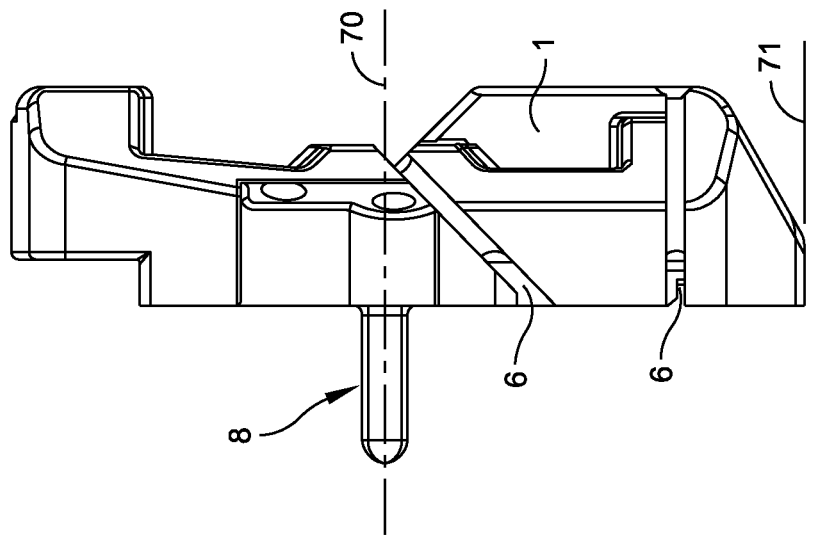
FIGS. 7A-7B are a plan view and a side view of the chamfer resection guide assembly 100 in a neutral position setting.
Figure 7A:
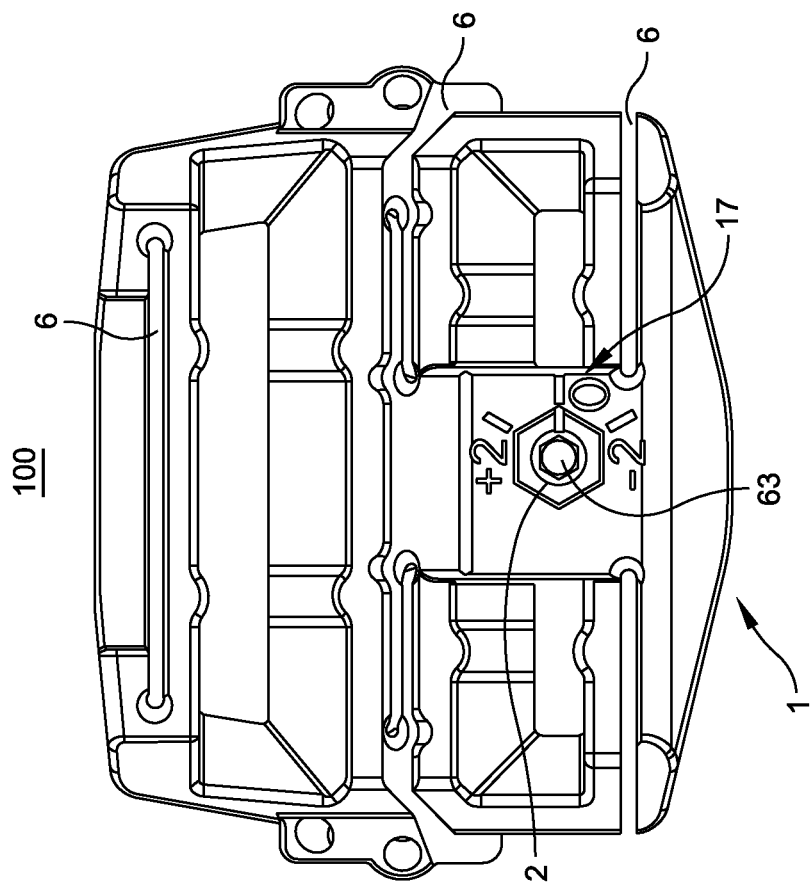
Figure 9B:
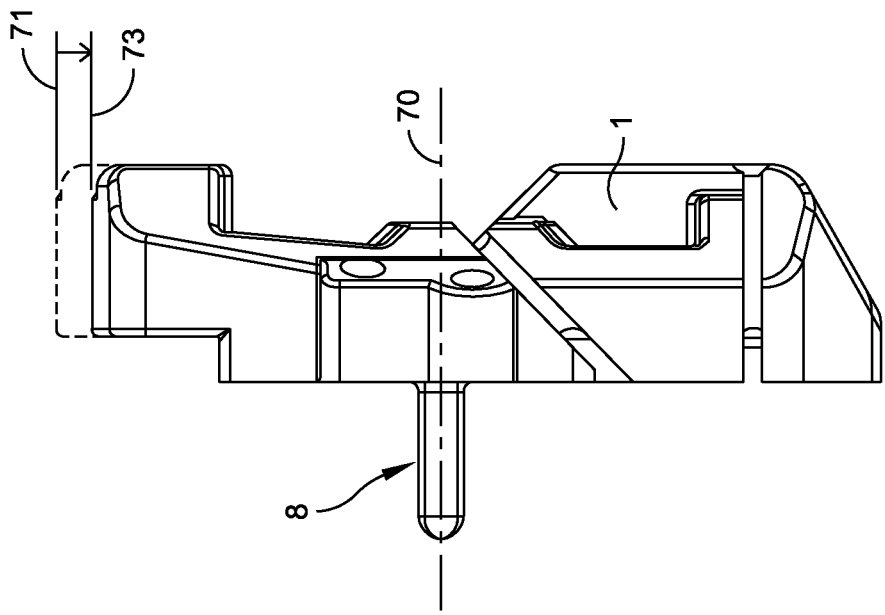
FIGS. 9A-9B are a plan view and a side view of the chamfer resection guide assembly 100 in a "−" position setting.
Figure 9A:
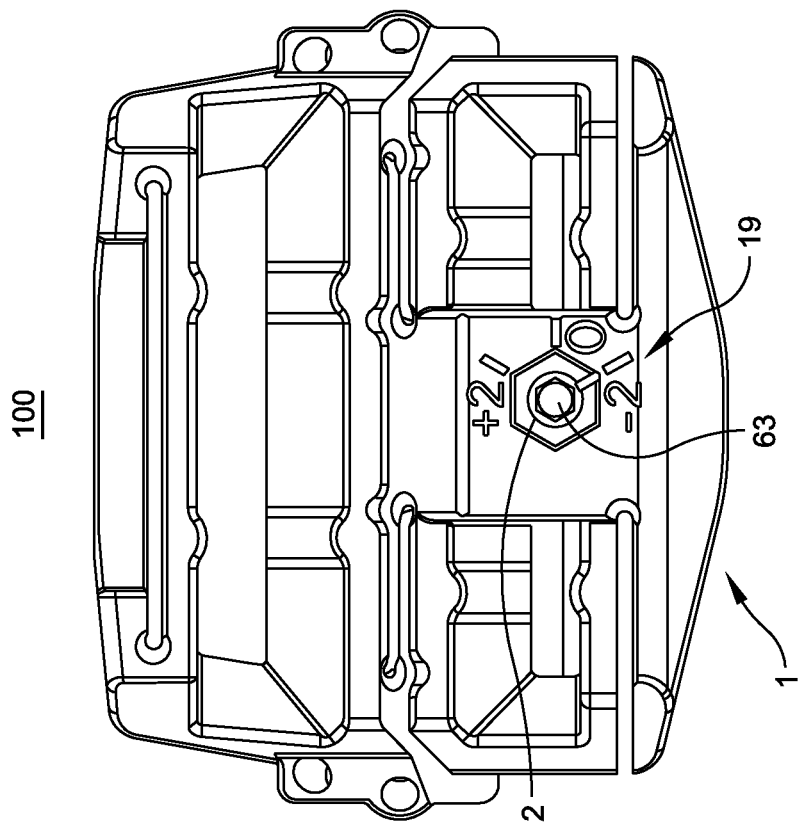

As shown in FIGS. 7A, 8A, 9A, the retaining lip 46 provided at the terminal end of the first blind hole 45 at the top side 30 of the block member forms a hexagonal opening and the first end 60 of the adjustment plunger 2 has a matching hexagonal shape that fits into the hexagonal opening. Normally, the coil spring 3 urges the adjustment plunger 2 against the retaining lip 46 and the hexagonal shape of the first end 60 and the opening formed by the retaining lip 46 keeps the first end 60 engaged in a locking manner with the retaining lip 46 and prevents the adjustment plunger 2 from turning about its longitudinal axis LL. The shape of the opening formed by the retaining lip 46 and the first end 60 of the adjustment plunger 2 does not need to be limited to a hexagonal shape but any number of non-circular shapes would provide the same functionality.

To adjust the position of the block member 1 with respect to the anchor member 5, the adjustment plunger 2 is pushed inward (i.e. away from the retaining lip 46 and towards the femoral contact surface 32) along its longitudinal axis LL compressing the coil spring 3. This disengages the first end 60 of the adjustment plunger 2 from the retaining lip 46 of the first blind hole 45 and unlocks the adjustment plunger 2 allowing it to be turned. In the illustrated example, the chamfer resection guide assembly 100 is configured to have three adjustment positions for the block member 1 using the hexagonal shape of the adjustment plunger 2 and the retaining lip 46 of the first blind hole 45.

Referring to FIGS. 7A-9B, the illustrated example chamfer resection guide 100 is configured with three positions "+2", "0" and "−2" noting the three possible positions for the block member 1 with respect to the anchor member 5. The position "0" marks the neutral or the initial position 17 (see FIG. 7A). FIG. 7B shows the relative position of the block member 1 with respect to the reference position 70 of the anchor member 5 marked by the reference features, the anchoring pins 8. Thus, the block member 1 and its resection guide slots 6 are in their neutral position 71 with respect to the reference position 70. Generally, the chamfer resection guide assembly 100 would be attached to the distal resection of a femur with the adjustment plunger 2 in the neutral position "0." Then, after the chamfer resection guide assembly 100 is attached to the distal resection of the femur by anchoring the anchor member 5 to the femur using reference features such as the anchoring pins 8, the position of the resection guide slots 6 can be adjusted from the neutral position by turning the adjustment plunger 2 to one of the two alternate positions, "+2" or "−2".

Referring to FIG. 8A, when the adjustment plunger 2 is depressed and rotated to the "+" offset position 18 as indicated on the block member 1, the block member 1 is shifted up in the anterior direction relative to the reference position 70 to its "+" offset position 72 as shown in FIG. 8B.

Referring to FIG. 9A, if adjustment plunger 2 is depressed and rotated to the "−" offset position 19, the block member 1 is shifted down in the posterior direction relative to the reference position 70 to its "−" offset position 73 as shown in FIG. 9B.

As discussed above, turning the adjustment plunger 2 results in the camming action of the offset cylinder boss 15, thus, sliding the block member 1 in one of the two directions noted by the arrow A in FIGS. 3 and 4. As discussed above, the amount of the linear displacement of the block member 1 is determined by the amount of the offset between the offset cylinder boss 15 and the cam body 4 and the amount of angular rotation made by the adjustment plunger 2 between the incremental adjustment positions. In the illustrated example, the incremental adjustment positions are separated by 60° by virtue of the hexagonal configuration of the first end 60 of the adjustment plunger 2. If a finer adjustment capability is desired, the first end 60 of the adjustment plunger 2 and the corresponding retaining lip 46 of the first blind hole 45 can be configured with shapes allowing finer incremental angular adjustment such as an octagon.

The camming action provided by the rotation of the camming member 20 about its rotational axis, the longitudinal axis LL, is shown in FIGS. 11A-11C. FIG. 11A shows the outlines of the cam body 4, the offset cylinder boss 15 and the blind slot 14 (shown in dotted line) in the "neutral" position. The blind slot 14 is configured with a dimension that the offset cylinder boss 15 fits within the blind slot 14 without undesirable space between the structures in the anterior/posterior directions (top to bottom direction as shown in FIGS. 11A-11C). FIG. 11A shows that the center 4c of the cam body 4 and the center 15c of the offset cylinder boss 15 are offset. The center 4c of the cam body 4 is aligned with the longitudinal axis LL of the camming member 20. FIG. 11B shows the adjusted configuration after the camming member 20 is turned in the "+" offset direction. The offset cylinder boss 15 has moved up and pushed the anchor member 5 up along with it as represented by the new position of the blind slot 14. FIG. 11C shows the adjusted configuration after the camming member 20 is turned in the "−" offset direction. The offset cylinder boss 15 has moved down and pushed the anchor member 5 down along with it as represented by the new position of the blind slot 14.

The first end 60 of the adjustment plunger 2 is preferably configured for receiving an adjustment tool, such as a screw driver or a wrench, that is used for pressing and turning the adjustment plunger 2. As shown in FIGS. 3 and 4, the first end 60 of adjustment plunger 2 according to the illustrated example is provided with a tool-receiving recess 63 for receiving a hex-key type tool.

The camming member operatively connects the block member and the anchor member and is configured for linearly displacing the anchor member and the block member with respect to each other for adjusting the position of the anchor member within the recessed region of the block member.

When the chamfer resection guide assembly 100 is attached to the distal end of a femur the anchor member 5 is sandwiched between the resected surface of the femoral bone and the block member 1. Thus, if the position of one or more of the guiding slots 6 is such that the anchor member 5 blocks one or more of the guiding slots 6, the anchor member may be provided with appropriate number of clearance cutouts 7 for allowing the saw blade of the cutting tool to extend through the anchor member 5 when resections are being made through the guiding slots 6. For example, in the illustrated embodiment, the clearance cutouts 7 provide clearance for the guiding slots 6a.

Figure 5B:
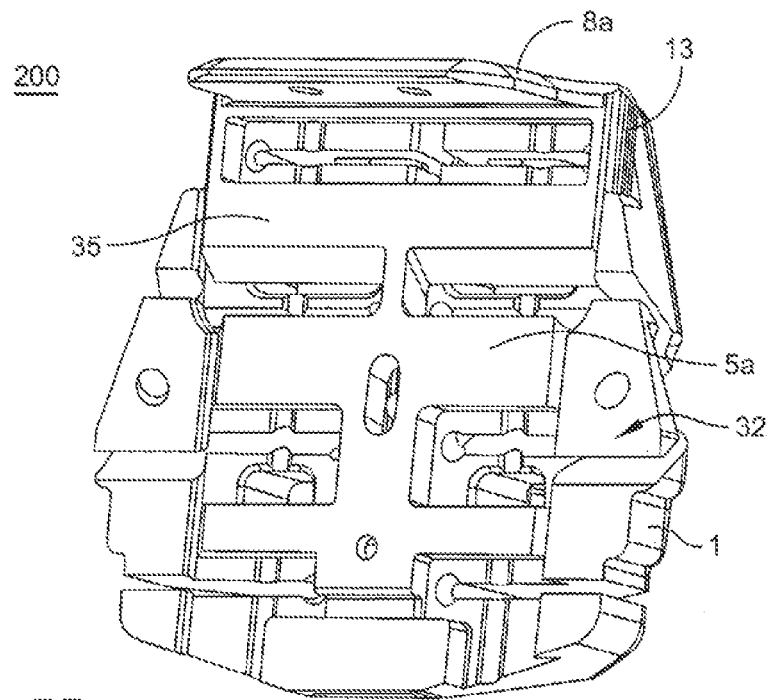
FIGS. 5B and 5C are isometric view and a side view, respectively, of a fully assembled chamfer resection guide assembly according to another embodiment.
Figure 5C:
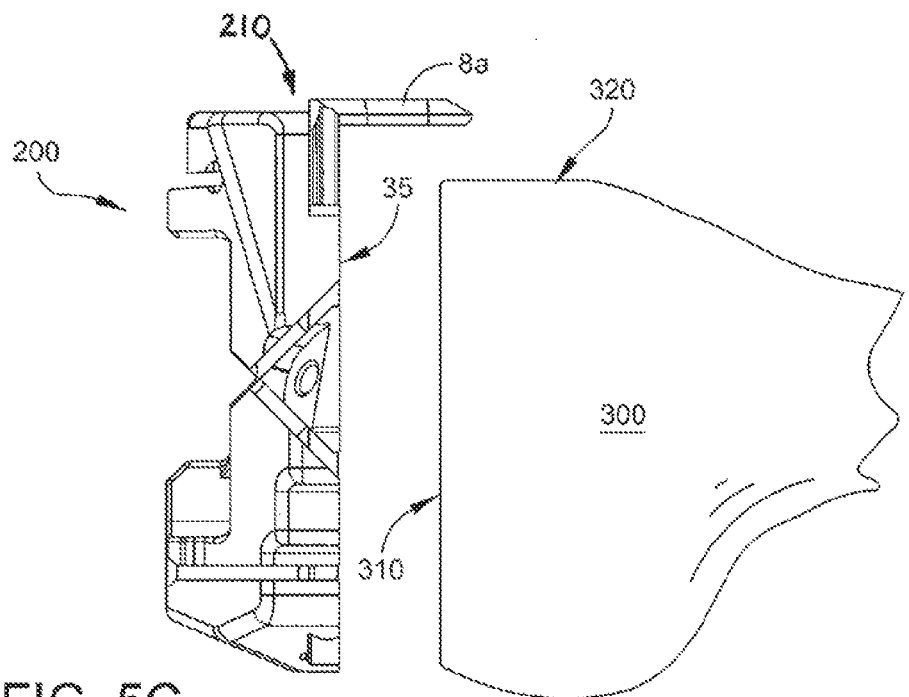
Figure 6:
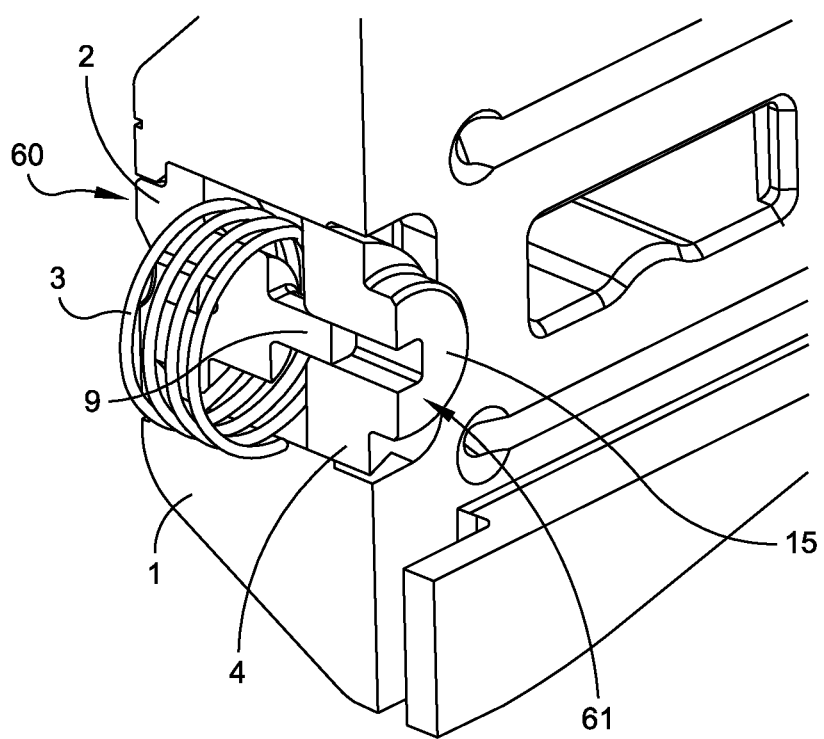
FIG. 6 is a detailed partial cross-sectional view of the camming member 20 situated in the block member 1 of the chamfer resection guide assembly 100.

Referring to FIGS. 5B and 5C, a chamfer resection guide assembly 200 according to another embodiment is shown. FIG. 5B shows the fully assembled chamfer resection guide assembly 200 and FIG. 5C shows a side view of the chamfer resection guide assembly 200 being attached to the resected distal surface 310 of a femur 300. The chamfer resection guide assembly 200 is configured for referencing the chamfer cuts to the resected anterior surface 320 of the femur 300. The anchor member 5a of this assembly does not have the anchoring pins 8 found on the anchor member 5 of the chamfer resection guide assembly 100. Instead, the anchor member 5a is provided with a footplate extension 8a that extends from the second femoral contacting surface 35 of the anchor member 5a near the anterior end 210 of the chamfer resection guide assembly 200. This configuration of anchor member 5a permits another means of using of the device that references position and orientation without impeding the means to saw through the device. Various other configurations of the anchor member, 5 or 5a, which perform the same referencing and functional tasks through other means not illustrated, may also be utilized.

The chamfer resection guide assembly 200 contacts the resected distal surface 310 of the femur 300 so that the second femoral contacting surface 35 of the anchor member 5a is flush against the resected distal surface 310 of the femur 300. With the second femoral contacting surface 35 contacting the resected distal surface 310 of the femur 300, the chamfer resection guide 200 is positioned to have the footplate extension 8a come in contact with the resected anterior surface 320 of the femur 300. This allows anterior referencing of the chamfer cuts effected with the chamfer resection guide assembly 200 because the positions of the chamfer guiding slots 6 are referenced against the resected anterior surface 320.

Unlike the existing resection guides that require repositioning of multiple instruments to adjust the position of the instrument in the anterior/posterior direction, the position of the chamfer resection guide of the present disclosure can be adjusted in the anterior/posterior direction without removing and repositioning the instrument. Thus, the chamfer resection guide of the present disclosure saves time and reduce potential error by leaving the appropriately chosen size chamfer resection guide in position and refining its final position through a mechanism that is conducive to a minimally invasive procedure. Other adjustment resection guides of a similar nature have large knobs that could interfere with soft tissue. The adjustment mechanism of the chamfer resection guide of the present disclosure is self-contained within the chamfer resection guide and also simultaneously functions to hold the assembly of the instrument together. Thus, the chamfer resection guide can be assembled without additional assembly processes such as crosspinning, welding, etc. This feature allows the assembly process for the instrument to be simpler and less costly.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention. The scope of the invention disclosed herein is to be limited only by the following claims.

What is claimed is:

1. A chamfer resection guide assembly for a distal total knee implant comprising:
    an anchor member for anchoring into a resected distal surface of a femur;

a block member including one or more cutting guide slots and a femoral contacting surface for placement against the resected distal surface of the femur, wherein the femoral contacting surface is provided with a recessed region in which the anchor member is slidably engaged therein; and a camming member operably connecting the block member and the anchor member and configured for linearly displacing the anchor member and the block member with respect to each other by a camming action;

wherein the block member is provided with a blind hole provided in the recessed region and the anchor member is provided with a blind slot, wherein the camming member is captured between the block member and the anchor member by engaging the blind hole and the blind slot, whereby turning the camming member about its longitudinal axis produces the camming action;

wherein the camming member has a first end and a second end and comprises:

an adjustment plunger provided at the first end and engaging the blind hole of the block member;

a cam body provided at the second end and engaging the blind slot of the anchor member; and a coil spring contained between the adjustment plunger and the cam body and urging the adjustment plunger against the block member and the cam body against the anchor member, wherein the adjustment plunger is configured with a mid-section that is larger in diameter than the first end and the second end, allowing the coil spring to be contained between the adjustment plunger and the cam body so that the mid-section interferes with a retaining lip of the blind hole to retain the adjustment plunger within the blind hole.

2. The chamfer resection guide assembly of claim 1, wherein the adjustment plunger and the cam body are configured to translate axially with respect to each other while rotating about the camming member's longitudinal axis in unison.

3. The chamfer resection guide assembly of claim 2, wherein the adjustment plunger and the cam body are coupled together by a mortise and tenon joint.

4. The chamfer resection guide assembly of claim 1, wherein the adjustment plunger is configured to engage the blind hole in a locking manner preventing the camming member from being rotated about its longitudinal axis when the adjustment plunger is urged against the block member.

5. The chamfer resection guide assembly of claim 4, wherein the adjustment plunger and the cam body are coupled together by a mortise and tenon joint.

6. The chamfer resection guide assembly of claim 4, wherein the cam body has a center aligned with the camming member's longitudinal axis; and an offset cylinder boss whose center is offset from the center of the cam body, wherein the offset cylinder boss engages the blind slot, wherein when the camming member rotates about its longitudinal axis, the offset cylinder boss produces the camming action.

7. The chamfer resection guide assembly of claim 1, wherein the adjustment plunger is configured to disengage the blind hole and be rotatable about its longitudinal axis when the adjustment plunger is pushed inward, compressing the coil spring.

8. The chamfer resection guide assembly of claim 7, wherein the block member has a top side and a second femoral contacting side, the blind hole being provided with the retaining lip at the top side of the block member wherein the retaining lip forms a non-circular terminal opening for the blind hole at the top side for engaging the first end of the camming member in a locking manner.

9. The chamfer resection guide assembly of claim 8, wherein the cam body has a center aligned with the camming member's longitudinal axis; and an offset cylinder boss whose center is offset from the center of the cam body, wherein the offset cylinder boss engages the blind slot, wherein when the camming member rotates about its longitudinal axis, the offset cylinder boss produces the camming action.

10. The chamfer resection guide assembly of claim 1, wherein the first end of the camming member is configured to receive a tool for turning the camming member.

11. The chamfer resection guide assembly of claim 1, wherein the anchor member is provided with a means for anchoring the chamber resection guide assembly to the resected distal surface of the femur, wherein the means for anchoring the chamber resection guide assembly comprises two anchoring pins.

* * * * *